(12) United States Patent
Ganachaud et al.

(10) Patent No.: US 10,358,541 B2
(45) Date of Patent: Jul. 23, 2019

(54) ORGANOPOLYSILOXANES AND METHODS FOR PREPARING SAME

(71) Applicants: ELKEM SILICONES FRANCE SAS, Lyons (FR); Institut National des Sciences Appliquées LYON, Villeurbanne (FR); Université Claude Bernard Lyon 1, Villeurbanne (FR); Centre national de la recherche scientifique, Paris (FR); UNIVERSITE JEAN MONNET SAINT ETIENNE, Saint-Etienne (FR)

(72) Inventors: François Ganachaud, Decines (FR); Etienne Fleury, Soucieu en Jarrest (FR); Daniel Portinha De Almeida, Fontaines sur Saône (FR); Aymeric Genest, Oullins (FR); Emmanuel Pouget, Lyons (FR)

(73) Assignees: ELKEM SILICONES FRANCE SAS, Lyons (FR); INSTITUT NATIONAL DES SCIENCES APPLIQUÉES LYON, Villeurbanne (FR); UNIVERSITÉ CLAUDE BERNARD LYON 1, Villeurbanne (FR); CENTRE NATIONAL DE LA RECHERCHE SCIENTIFIQUE, Paris (FR); UNIVERSITE JEAN MONNET SAINT ETIENNE, Saint-Etienne (FR)

( * ) Notice: Subject to any disclaimer, the term of this patent is extended or adjusted under 35 U.S.C. 154(b) by 0 days.

(21) Appl. No.: 15/537,132

(22) PCT Filed: Dec. 21, 2015

(86) PCT No.: PCT/EP2015/080843
§ 371 (c)(1),
(2) Date: Jun. 16, 2017

(87) PCT Pub. No.: WO2016/102498
PCT Pub. Date: Jun. 30, 2016

(65) Prior Publication Data
US 2018/0265668 A1 Sep. 20, 2018

(30) Foreign Application Priority Data
Dec. 22, 2014 (FR) ..................... 14 63055

(51) Int. Cl.
*C08K 3/36* (2006.01)
*A61Q 19/00* (2006.01)
*C08G 85/00* (2006.01)
*C08K 5/09* (2006.01)
*C08K 5/10* (2006.01)
(Continued)

(52) U.S. Cl.
CPC ............... *C08K 3/36* (2013.01); *A61K 8/898* (2013.01); *A61Q 19/00* (2013.01); *C08G 77/38* (2013.01); *C08G 77/388* (2013.01); *C08G 85/002* (2013.01); *C08G 85/004* (2013.01); *C08K 5/09* (2013.01); *C08K 5/10* (2013.01); *A61K 2800/10* (2013.01); *C08G 77/26* (2013.01); *C08G 2261/728* (2013.01)

(58) Field of Classification Search
CPC ... C08K 3/36; C08K 5/09; C08K 5/10; C08G 85/002; C08G 85/004; C08G 77/388; C08G 77/38
See application file for complete search history.

(56) References Cited

U.S. PATENT DOCUMENTS 3,033,815 A 5/1962 Pike et al.
5,990,334 A 11/1999 Hierstetter et al.
(Continued)

FOREIGN PATENT DOCUMENTS

JP 20000000888 1/2000
JP A-2007535605 12/2007
(Continued)

OTHER PUBLICATIONS

International Search Report for PCT/EP2015/080843, dated Mar. 9, 2015.
(Continued)

*Primary Examiner* — Peter D. Mulcahy
(74) *Attorney, Agent, or Firm* — B. Aaron Schulman, Esq.; Stites & Harbison, PLLC

(57) ABSTRACT

The present invention concerns an organopolysiloxane (A) able to be obtained by the reaction, at a temperature of between 10° C. and 75° C., between—at least one compound (C) chosen from the organic compounds comprising at least one alkene or alkyne functional group, at least one of the substituents of which is an acid functional group and the organic compounds comprising at least one acid functional group and at least one alkene or alkyne functional group, at least one of the substituents of which is an electron-withdrawing group; and—at least one organopolysiloxane (B) chosen from the organopolysiloxanes comprising siloxyl units (I.1) and (I.2) of the following formulae: (I) The present invention also concerns compositions comprising said organopolysiloxanes (A) and the uses thereof.

(I)

$$Y_a Z_b^1 SiO_{\frac{4-(a+b)}{2}};$$ (I.1)

$$Z_c^2 SiO_{\frac{4-c}{2}}$$ (I.2)

21 Claims, No Drawings

(51) Int. Cl.
    *C08G 77/388*     (2006.01)
    *A61K 8/898*     (2006.01)
    *C08G 77/38*     (2006.01)
    *C08G 77/26*     (2006.01)

(56) References Cited

U.S. PATENT DOCUMENTS

| | | |
|---|---|---|
| 6,124,490 A | 9/2000 | Gormley et al. |
| 6,177,511 B1 | 1/2001 | Dauth et al. |
| 6,228,967 B1 | 5/2001 | Fost et al. |
| 8,728,225 B2 | 5/2014 | Standke et al. |
| 8,979,996 B2 | 3/2015 | Standke et al. |
| 2008/0138301 A1 | 6/2008 | Gormley et al. |
| 2012/0037040 A1 | 2/2012 | Standke et al. |
| 2014/0208981 A1 | 7/2014 | Standke et al. |

FOREIGN PATENT DOCUMENTS

| | | |
|---|---|---|
| JP | 2012-524163 | 10/2012 |
| WO | WO-2005111115 | 11/2005 |

OTHER PUBLICATIONS

Mather, et al, "Michael addition reaction in macromolecular design for emerging technologies", 2006, pp. 487-531, vol. 31, Prog. Polym. Sci.

ORGANOPOLYSILOXANES AND METHODS FOR PREPARING SAME

The present invention relates to an organopolysiloxane (A), to its preparation method, to compositions comprising it and to its use notably as an adhesion promoter, an anti-mist additive, an anti-foam additive, an electric conductor, an antistatic additive, an antibacterial additive, an anti-corrosion additive, an anti-fire additive or for coating in a thin layer.

Many approaches have been developed for proposing modified organopolysiloxane compounds. As the object was to provide organopolysiloxane compounds with various viscoelastic properties in order to adapt to diverse uses, notably as an elastomer, in a paper or film coating composition, as an adhesion promoter, as an anti-mist additive, etc. Therefore there is an interest of providing organopolysiloxane compounds having viscoelastic properties which may be modulated in order to adapt to any type of use.

There is also an interest for providing a simple and economical method allowing the preparation of organopolysiloxane compounds having viscoelastic properties which may be modulated.

These objects are fulfilled by the present application which relates to an organopolysiloxane (A) which may be obtained by reaction, at a temperature comprised between 10° C. and 75° C., between:
- at least one compound (C) selected from among the organic compounds comprising at least one alkene or alkyne function for which at least one of the substituents is an acid function and the organic compounds comprising at least one acid function and at least one alkene or alkyne function for which at least one of the substituents is an electroattractor group; and
- at least one organopolysiloxane (B) selected from among organopolysiloxanes comprising siloxyl units (I.1) and (I.2) of the following formulae:

 (I.1)

 (I.2)

wherein:
a=1 or 2, b=0, 1 or 2 and a+b=1, 2 or 3
c=1, 2, 3 or 4
the symbols Y, identical or different, represent a functional group of formula (I.3):

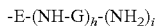 (I.3)

wherein:
h=0 or 1;
i=0 or 1;
h+i=1 or 2
E represents an aliphatic, cycloaliphatic or aromatic divalent hydrocarbon radical comprising from 1 to 30 carbon atoms; preferably aliphatic containing from 1 to 10 carbon atoms;
when it is present, G represents an aliphatic hydrocarbon radical comprising from 1 to 10 carbon atoms, monovalent when i=0 or divalent when i=1;
the symbols $Z^1$ and $Z^2$, either identical or different, represent a monovalent hydrocarbon radical having from 1 to 30 carbon atoms and optionally comprising one or several unsaturations and/or one or several fluorine atoms, a hydroxyl group, or a radical-$OR^1$ with $R^1$ which represents a linear, cyclic or branched $C_1$-$C_{10}$ hydrocarbon radical, and preferably $Z^1$ and $Z^2$ represent a monovalent hydrocarbon group selected from among the group formed by alkyl groups having from 1 to 8 carbon atoms, alkenyl groups having from 2 to 6 carbon atoms and aryl groups having from 6 to 12 carbon atoms optionally comprising one or several fluorine atoms, a hydroxyl group, a radical-$OR^1$ with $R^1$ which represents a linear, cyclic or branched $C_1$-$C_{10}$ hydrocarbon radical, and even more preferentially selected from among the group formed by a methyl, ethyl, propyl, 3,3,3-trifluoropropyl, vinyl, hydroxyl, ethoxyl, methoxyl, xylyl, tolyl and phenyl group; said polyorganosiloxane (B) comprising, per molecule, at least a siloxyl unit (I.1) bearing at least a functional group of formula (I.3).

According to a particular embodiment, the organopolysiloxane (A) as described above is obtained at a reaction temperature comprised between 10 and 70° C., preferably between 15 and 70° C.

Within the scope of the present invention, by electroattractor is meant a group attracting to it electrons, i.e. an atom or a group of atoms having greater electronegativity than that of hydrogen, thereby resulting in electron-depleted bonds. Thus, within the scope of the invention, the electroattractor group depletes the alkene or alkyne functions in electrons. A definition of such groups is notably given in the publication "Michael addition reactions in macromolecular design for emerging technologies" Progress in Polymer Science 31 (5), 487-531(2006). From among electroattractor groups, mention may notably be made of ketone, acid, amide, phosphonate ester, phosphonic acid, sulfonic acid, sulfone, ester, thioester, $NO_2$ group, CN group, functions etc.

Within the scope of the present application, by acid function are notably meant carboxylic acid, sulfonic acid and phosphonic acid functions. Thus and preferably, the compound (C) of the present invention is selected from organic compounds comprising at least one double or triple carbon-carbon bond for which at least one of the substituents is a carboxylic acid, sulfonic acid or phosphonic acid function or the organic compounds comprising at least one acid function selected from among a carboxylic acid function, a sulfonic acid function or a phosphonic acid function and at least one double or triple carbon-carbon bond for which at least one of the substituents is an electroattractor group. This compound C may then react according to an Aza-Michael reaction with primary or secondary amines as described in the publication «Michael addition reactions in macromolecular design for emerging technologies» Progress in Polymer Science 31 (5), 487-531(2006). Preferably, the compound (C) according to the invention comprises at least one double carbon-carbon bond for which at least one of the substituents is a carboxylic acid function or comprises at least one carboxylic acid function and at least one double carbon-carbon bond for which at least one of the substituents is an electroattractor group. Still more preferentially, in the compound (C) according to the invention at least one of the double carbon-carbon bonds and at least one of the acid functions are conjugate.

From among these compounds, mention may preferably be made of the compounds of formula (II):

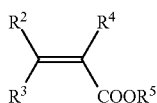
(II)

wherein:
R², R³ and R⁴, either identical or different, represent a hydrogen atom, a COOH group or a $C_1$-$C_6$, preferably $C_1$-$C_3$ alkyl group, preferably a methyl group;
R⁵ represents a hydrogen atom, an alkyl group or an aryl group, wherein the alkyl and the aryl comprise at least a COOH group.

Preferably, in the compounds of formula (II),
R² and R³, either identical or different, represent a hydrogen atom or a $C_1$-$C_6$, preferably $C_1$-$C_3$ alkyl group, preferably a methyl group;
R⁴ represents a hydrogen atom, a $C_1$-$C_6$, preferably $C_1$-$C_3$ alkyl group, preferably a methyl group, or a COOH group;
R⁵ represents a hydrogen atom, an alkyl group or an aryl group, wherein the alkyl and the aryl comprise at least one COOH group.

Preferably, the compounds (C) of the invention are selected from among acrylic acid, methacrylic acid, itaconic acid, crotonic acid, 2-carboxyethylacrylate, 3-carboxypropylacrylate, maleic acid, fumaric acid, 2-(acryloyloxy)acetic acid, 2-(acryloyloxy)propanoic acid, 3-(acrylolyloxy)propanoic acid, 2-(acryloyloxy)-2-phenylacetic acid, 4-(acryloyloxy)butanoic acid, 2-(acryloyloxy)-2-methylpropanoic acid, 5-(acryloyloxy)pentanoic acid, (E)-but-2-enoic acid, (Z)-prop-1-ene-1,2,3-tricarboxylic acid, cinnamic acid, sorbic acid, 2-hexenoic acid, 2-pentenoic acid, 2,4-pentadienoic acid, ethenesulfonic acid, vinylphosphonic acid, (1-phenylvinyl)phosphonic acid, 3-(vinylsulfonyl)propanoic acid, 2-(vinylsulfonyl)acetic acid, 2-(vinylsulfonyl)succinic acid, acetylene dicarboxylic acid and propiolic acid.

Preferably, the compounds (C) of the invention are selected from acrylic acid, methacrylic acid, itaconic acid, crotonic acid, 2-carboxyethylacrylate, 3-carboxypropylacrylate, maleic acid and fumaric acid.

Preferably, the compound (C) is acrylic acid or 2-carboxyethylacrylate.

Preferably, the compound (C) is acrylic acid.

Preferably, the organopolysiloxanes (B) may have a linear, branched, or cyclic structure. When these are linear organopolysiloxanes, the latter essentially consist of siloxyl units «D», notably selected from the group formed by siloxyl units $Y_2SiO_{2/2}$, $YZ^1SiO_{2/2}$ and $Z^2_2SiO_{2/2}$ and siloxyl units «M», notably selected from among the group formed by siloxyl units $Y_3SiO_{1/2}$, $YZ^1_2SiO_{1/2}$, $Y_2Z^1SiO_{1/2}$ and $Z^2_3SiO_{1/2}$, the Y, $Z^1$ and $Z^2$ being as defined above, it being understood that the polyorganosiloxane (B) comprises, per molecule, at least one siloxyl unit bearing at least one functional group of formula (I.3) defined above. In a particularly preferred embodiment, the organopolysiloxanes (B) are selected from the organopolysiloxanes comprising siloxyl units (I.1) and (I.2) of the following formulae:

(I.1)

(I.2)

wherein:
Y and $Z^1$ and $Z^2$ have the definitions given above;
a=1 or 2, b=0, 1 or 2 and a+b=2 or 3
c=1 or 2.

In a particularly preferred way, the organopolysiloxanes (B) are selected from among the organopolysiloxanes comprising units (I.1) selected from the group formed by $YZ^1SiO_{2/2}$ and $YZ^1_2SiO_{1/2}$ and units (I.2) selected from the group formed by $Z^2_2SiO_{2/2}$ and $Z^2_3SiO_{1/2}$, the Y, $Z^1$ and $Z^2$ being such as defined above, it being understood that the polyorganosiloxane (B) comprises, per molecule, at least one siloxyl unit (I.1) bearing at least a functional group of formula (I.3) defined above.

Preferably, the organopolysiloxanes (B) have a degree of polymerization comprised between 2 and 5,000, preferably between 2 and 1,500, more preferably between 2 and 500.

Preferably, the organopolysiloxanes (B) comprise a number of siloxyl units (I.1) comprised between 1 and 100, preferably between 2 and 80.

Preferably, the organopolysiloxanes (B) comprise an amount of NH bond/gram comprised between $1·10^{-5}$ and $1·10^{-1}$ mol/g, and preferably between $5·10^{-5}$ and $5·10^{-2}$ mol/g.

Preferably, the organopolysiloxanes (B) may be selected from among the compounds of formula:

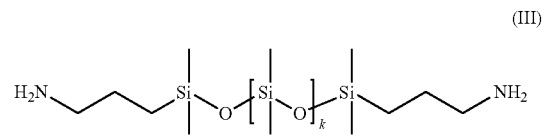
(III)

with k=1 to 1000, preferably 1 to 800

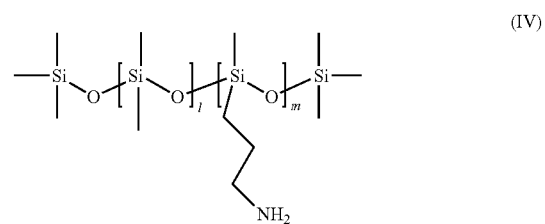
(IV)

with l=1 to 1000, preferably 1 to 800 and m=1 to 150, preferably 1 to 100;

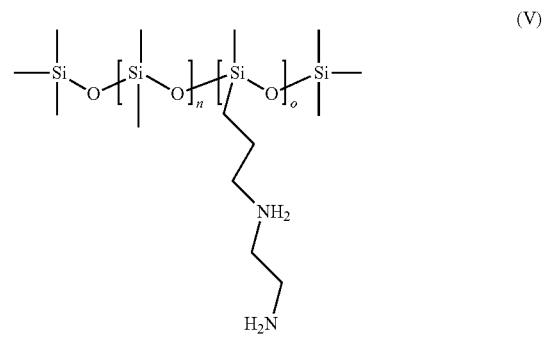
(V)

with n=1 to 1,000, preferably 1 to 800 and o=1 to 150, preferably 1 to 100;

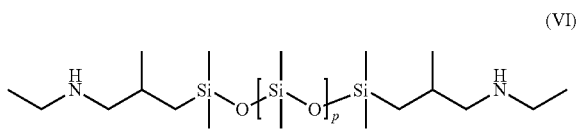

(VI)

with p=1 to 1,000, preferably 1 to 800.

According to another embodiment, the organopolysiloxane (B) may be selected from among the compounds of formula (IV) and (V) as described above with terminal units dimethylmethoxysilyl or dimethylethoxysilyl instead of trimethylsilyl.

In a particular embodiment, the organopolysiloxane (B) may be as an emulsion.

All the preferred characteristics defining the organopolysiloxanes (B) may be combined with each other.

Generally, the ratio r representing the ratio between the number of moles of alkene or alkyne function of the compound (C) may be defined for which at least one of the substituents is an electroattractor group or an acid function, preferably the number of moles of the double bond C=C or C≡C for which at least one of the substituents is an electroattractor group or an acid function, and the number of moles of N—H bonds borne by the organopolysiloxane (B). The ratio r corresponds to the following relationship:

$$r = \frac{n(C=C, C\equiv C)}{n(N-H)}$$

It is also possible to define the ratio J representing the ratio between the number of moles of acid functions of the compound (C) and the number of moles of amine functions of the organopolysiloxane (B). The ratio J corresponds to the following relationship:

$$J = \frac{\text{number of moles of the compound (C)} \times \text{number of acid functions of the compound (C)}}{\text{number of moles of the compound (B)} \times \text{number of amine functions of the compound (B)}}$$

By amine function, are meant primary or secondary amines. It should therefore be understood that a mole of a primary amine function contains two moles of N—H bonds and that a mole of secondary amine function contains one mole of N—H bonds.

Preferably, the ratio J is comprised between 0.01 and 20, preferably between 0.5 and 3 and still more preferentially between 0.5 and 1.5.

Preferably, the ratio r is comprised between 0.01 and 10, preferably between 0.05 and 2, and still more preferentially between 0.2 and 1.5.

Preferably, the ratio J is comprised between 0.01 and 20, preferably between 0.5 and 3, still more preferentially between 0.5 and 1.5 and the ratio r is comprised between 0.01 and 10, preferably between 0.05 and 2 and still more preferentially between 0.2 and 1.5. Preferably, the organopolysiloxane (B) has a dynamic viscosity measured at 25° C. with a rheometer with imposed stress, notably TA-DHRII, comprised between 1 and 100,000 mPa·s, preferably between 100 and 50,000 mPa·s.

In a particularly advantageous way, because of the method applied, the organopolysiloxane (A), has a dynamic viscosity measured at 25° C. with a rheometer with imposed stress, notably TA-DHRII, at least 10 times greater than that of the organopolysiloxane (B).

The organopolysiloxane (A) may optionally appear as an emulsion.

The organopolysiloxanes (A) obtained may be viscoelastic liquids or viscoelastic solids. This may be referred as a gel when the organopolysiloxane (A) is at the transition between a viscoelastic liquid and solid. It is thus possible to obtain organopolysiloxanes (A) having viscoelastic properties which may be modulated.

The present invention also relates to a method for preparing an organopolysiloxane (A) comprising the putting into contact, at a temperature comprised between 10 and 75° C., between:

at least one compound (C) selected from among the organic compounds comprising at least one alkene or alkyne function for which at least one of the substituents is an acid function and the organic compounds comprising at least one acid function and at least one alkene or alkyne function for which at least one of the substituents is an electroattractor group; and at least an acid function, and at least an organopolysiloxane (B) comprising siloxyl units (I.1) and (I.2) of the following formulae:

$$Y_a Z^1_b SiO_{\frac{4-(a+b)}{2}};$$ (I.1)

$$Z^2_c SiO_{\frac{4-c}{2}}$$ (I.2)

wherein:
a=1 or 2, b=0, 1 or 2 and a+b=1, 2 or 3
c=1, 2, 3 or 4
the symbols Y, either identical or different represent a functional group of formula (I.3):

$$\text{-E-(NH-G)}_h\text{-(NH}_2)_i$$ (I.3)

wherein:
h=0 or 1;
i=0 or 1;
h+i=1 or 2
E represents an aliphatic, cycloaliphatic or aromatic divalent hydrocarbon radical comprising from 1 to 30 carbon atoms; preferably aliphatic containing from 1 to 10 carbon atoms;
when it is present, G represents an aliphatic hydrocarbon radical comprising from 1 to 10 carbon atoms, monovalent when i=0 or divalent when i=1;
the symbols $Z^1$ and $Z^2$, either identical or different, represent a monovalent hydrocarbon radical having from 1 to 30 carbon atoms and optionally comprising one or several unsaturations and/or one or several fluorine atoms, a hydroxyl group, or a radical-$OR^1$ with $R^1$ which represents a linear, cyclic or branched $C_1$-$C_{10}$ hydrocarbon radical and preferably $Z^1$ and $Z^2$ represent a monovalent hydrocarbon group selected from among the group formed by the alkyl groups having from 1 to 8 carbon atoms, the alkenyl groups having from 2 to 6 carbon atoms and the aryl groups having from 6 to 12 carbon atoms optionally comprising one or several fluorine atoms, a hydroxyl group, or a radical-$OR^1$, with $R^1$ which represents a linear, cyclic or branched $C_1$-$C_{10}$ hydrocarbon radical, and even more preferentially selected from among the group formed by a methyl, ethyl, propyl, 3,3,3-trifluoropropyl, vinyl, hydroxyl, ethoxyl, methoxyl, xylyl, tolyl and phenyl group; said polyorganosiloxane (B) comprising, per molecule at least one siloxyl unit (I.1) bearing at least one functional group of formula (I.3).

According to an alternative of the method, the compound (C) and the organopolysiloxane (B) are put into contact at a temperature strictly less than 10° C., so as to avoid heating of the reaction medium, and the temperature of the reaction medium is then gradually brought to a temperature comprised between 10 and 75° C.

Without intending to be bound to any theory, the method of the present invention results in an Aza-Michael reaction between the NH bonds borne by the organopolysiloxane (B) and the alkene or alkyne functions of the compound (C). The compound (C) also comprising at least one acid function, the method of the invention also applies an acid-based reaction generating ionic bonds between the amine functions of the organopolysiloxane (B) and said acid functions of the compound (C). These ionic bonds give the organopolysiloxane (A) a supermolecular nature.

When the method is applied at temperatures above 75° C., reactions may lead to the formation of products which are not desired.

In a particularly advantageous way, the association of both of these reactions, gives the possibility of obtaining an organopolysiloxane (A) for which the viscosity measured at 25° C., with a rheometer with imposed stress, notably TA-DHRII, is at least 10 times greater than that of the organopolysiloxane (B).

According to the different applications of the method of the invention (selection of the organopolysiloxane (B), selection of the reaction conditions (reaction time, temperature, ratio of reagent . . . )), the organopolysiloxane (A) obtained may be a viscoelastic liquid or a viscoelastic solid. This may be referred to as a gel when the organopolysiloxane (A) is at the transition between a viscoelastic liquid and solid. It is thus possible to obtain organopolysiloxanes (A) having viscoelastic properties which may be modulated.

Within the scope of the present invention, by Aza-Michael reaction is meant the amine addition reaction on multiple carbon-carbon bonds, notably alkene or alkyne functions, and more preferentially double carbon-carbon bonds.

The compound (C) and the organopolysiloxanes (B) and (A) are as defined above.

The duration of the putting into contact between the compound (B) and the compound (C) is variable, comprised between a few minutes or a few hours and several days. It depends on the nature of the compounds (B) and (C) as well as on the temperature at which they are put into contact. One skilled in the art will be able to adapt this duration, notably by following the advance of the reaction by analytical methods like $^1$H NMR.

The organopolysiloxane (B) may be obtained by reaction between an organopolysiloxane comprising at least one hydroxyl group and an alkoxysilane comprising at least one functional group of formula (I.3) as described above.

According to an embodiment of the method according to the invention, the organopolysiloxane (B) may be prepared insitu in the presence of the compound (C).

Preferably, the method of the present invention is applied at a temperature comprised between 10 and 70° C., preferably between 15 and 70° C.

According to a preferential mode, the method of the invention is applied at atmospheric pressure.

The method may be applied in the presence of microwave and/or ultrasonic irradiation.

The method according to the invention may be applied in air but also under the atmosphere of an inert gas such as argon or nitrogen.

In a particularly advantageous way, the method of the present invention may be applied in bulk or in the presence of a solvent. The solvent is notably selected from among:
  protic polar solvents, such as for example water, alcohols, ionic liquids;
  apolar solvents such as for example heptane, toluene, methylcyclohexane;
  aprotic polar solvents such as ketones (for example acetone), ethers, esters, tetrahydrofurane (THF), dimethylsuifoxide (DMSO), dimethylformamide (DMF).

Preferably, the method of the invention is applied in the absence of solvent (in bulk).

The method of the present invention may be applied in the presence of a catalyst, notably selected from among basic, acid, nucleophilic or organometal catalysts.

The method of the invention may also be applied in the presence of a filler.

Within the scope of the present invention, the fillers are preferably mineral fillers. They may notably be siliceous fillers. As these are siliceous materials, they may play the role of a reinforcing or semi-reinforcing charge. The reinforcing siliceous fillers are selected from colloidal silicas, combustion silica powders and precipitation silica powders or mixtures thereof. These powders have an average particle size generally less than 0.1 µm (micrometers) and a BET specific surface area greater than 30 m$^2$/g, preferably comprised between 30 and 350 m$^2$/g. The semi-reinforcing siliceous fillers such as diatomaceous earths or milled quartz, may also be used. As regards the non-siliceous mineral materials, they may intervene as a semi-reinforcing or stuffing mineral filler. Examples of these non-siliceous fillers which may be used alone or as a mixture are carbon black, titanium dioxide, aluminium oxide, alumina hydrate or aluminium trihydroxide, expansed vermiculite, non-expansed vermiculite, calcium carbonate optionally treated at the surface with fatty acids, zinc oxide, mica, talcum, iron oxide, kaolin, barium sulfate and slaked lime. These fillers have a grain size generally comprised between 0.001 and 300 µm (micrometers) and a BET surface area of less than 100 m$^2$/g. Practically, but with no limitation, the fillers used may be a mixture of quartz and silica. The fillers may be treated by any suitable product.

The filler may be introduced either directly mixed with the organosiloxane (B) or into the reaction medium after mixing the organosiloxane (B) and the compound (C).

As regards weight, application of an amount of filler comprised between 1% and 50% by weight is preferred, preferably between 1% and 30% by weight based on the whole of the constituents (B) and (C) and even more preferentially from 1% to 10% by weight based on the whole of the constituents (B) and (C).

Preferably, within the scope of the method of the present invention, the ratio J, as defined above, is comprised between 0.01 and 20, preferably between 0.5 and 3 and even more preferentially between 0.5 and 1.5.

Preferably, within the scope of the method of the present invention, the ratio r, as defined above, is comprised between 0.01 and 10, preferably between 0.05 and 2, and still more preferentially between 0.2 and 1.5.

Preferably, within the scope of the method of the present invention, the ratio J, as defined above, is comprised between 0.01 and 20, preferably between 0.5 and 3, still more preferentially between 0.5 and 1.5 and the ratio r, is comprised between 0.01 and 10, preferably between 0.05 and 2 and still more preferentially between 0.2 and 1.5.

The present invention also relates to a composition K1 comprising at least one organopolysiloxane (A) according to the invention. Preferably, the composition K1 may be an organopolysiloxane composition. The composition K1 may further comprise at least one filler and/or at least one organopolysiloxane.

The composition K1 may also comprise one or several usual functional additives. As usual functional additive families, mention may be made of:
silicone resins;
adherence promoters or modulators;
additives for increasing consistency;
pigments,
thermal strength additives, oil strength or fire strength additives, for example metal oxides.

The composition K1 may also comprise an organopolysiloxane comprising at least one carboxylic function.

The composition K1 may also comprise at least an organopolysiloxane (B) as defined above.

In a particularly advantageous way, as specified above, the organopolysiloxane (A) has a higher dynamic viscosity than that of the initial organopolysiloxane (B). Consequently, these organopolysiloxanes (A) may be used in the same applications as silicone elastomers, or further in the same applications than silicone gels, for example for wound care (coating of bandages, manufacturing of external prosthesis, anti-scar cushions), or for the encapsulation of electronic components or as coatings, notably for coating flexible films in paper or plastic as well as for textile coating (airbag).

The organopolysiloxanes (A) may also be used as additives and notably as additives promoting adhesion, anti-mist, anti-foam, antistatic, antibacterial, anti-corrosion, anti-fire, anti-graffiti additives or for temporary printing, for thin layer coating, or in different compositions.

As an illustration and not as a limitation, these organopolysiloxanes (A) and the compositions K1 comprising them may be used in different applications like paints, coatings, adhesives, sealants, personal care, health care, textile treatment, electronics, automobile, rubbers, anti-foam compositions, etc.

The present invention also relates to a composition X for preparing an organopolysiloxane (A) according to the invention, comprising:
at least one compound (C) selected from among the organic compounds comprising at least a alkene or alkyne function for which at least one of the substituents is an acid function and the organic compounds comprising at least an acid function and at least an alkene or alkyne function for which at least one of the substituents is an electroattractor group; and
at least one organopolysiloxane (B) comprising siloxyl units (I.1) and (I.2) of the following formulae:

  (I.1)

  (I.2)

wherein:
a=1 or 2, b=0, 1 or 2 and a+b=1, 2 or 3
c=1, 2, 3 or 4 the symbols Y, either identical or different, represent a functional group of formula (I.3):

  (I.3)

wherein:
h=0 or 1;
i=0 or 1;
h+i=1 or 2
E represents an aliphatic, cycloaliphatic or aromatic divalent hydrocarbon radical comprising from 1 to 30 carbon atoms; preferably aliphatic containing from 1 to 10 carbon atoms;
when it is present, G represents an aliphatic hydrocarbon radical comprising from 1 to 10 carbon atoms, monovalent when i=0 or divalent when i=1;
the symbols $Z^1$ and $Z^2$, either identical or different, represent a monovalent hydrocarbon radical having from 1 to 30 carbon atoms and optionally comprising one or several unsaturations and/or one or several fluorine atoms, a hydroxyl group, or a radical-$OR^1$ with $R^1$ which represents a linear, cyclic or branched $C_1$-$C_{10}$ hydrocarbon radical, and preferably $Z^1$ and $Z^2$ represent a monovalent hydrocarbon group selected from among the group formed by alkyl groups having from 1 to 8 carbon atoms, alkenyl groups having from 2 to 6 carbon atoms and aryl groups having from 6 to 12 carbon atoms optionally comprising one or several fluorine atoms, a hydroxyl group, or a radical-$OR^1$ with $R^1$ which represents a linear, cyclic or branched $C_1$-$C_{10}$ hydrocarbon radical, and still more preferentially selected from among the group formed by a methyl, ethyl, propyl, 3,3,3-trifluoropropyl, vinyl, hydroxyl, ethoxyl, methoxyl, xylyl, tolyl and phenyl; said polyorganosiloxane (B) comprising, per molecule, at least one siloxyl unit (I.1) bearing at least one functional group of formula (I.3).

The compound (C) and the organopolysiloxanes (A) and (B) being as defined above.

The present invention will now be described by means of non-limiting examples.

EXAMPLES

In the examples below, given as an illustration, reference is made to the following definitions:
Mn represents the number average molar mass.
PDMS=polydimethylsiloxane.
The PDMSes applied in the following examples fit one of the following formulae:

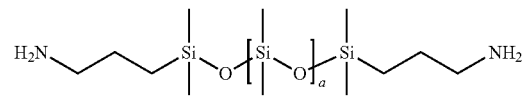

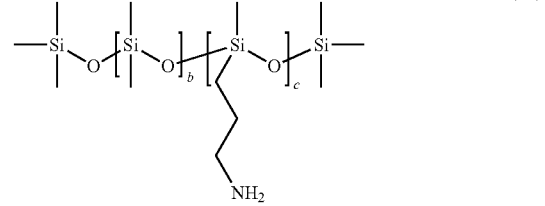

-continued

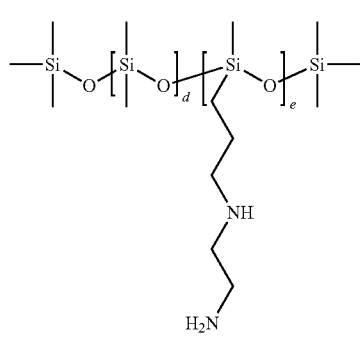

(V)

ORGANOSILOXANE (1):

N-(2-aminoethyl)-3-aminopropylmethylbis(trimethylsiloxy)silane

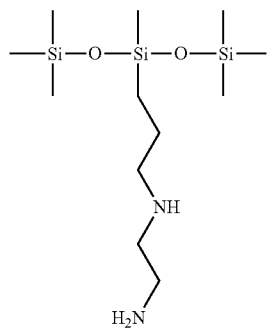

ORGANOSILOXANE (2): Commercial, Gelest SIA0604.5

3-aminopropylmethylbis(trimethylsiloxy)silane

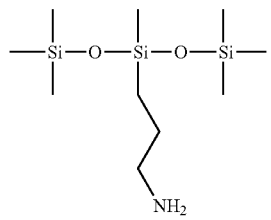

PDMS(3): Gelest, Mn≈3000 g/mol; compound of formula (III); amount of N—H bonds per gram=$1.33 \cdot 10^{-3}$ mol/g;

PDMS(4): Gelest; a compound of formula (III) amount of N—H bond per gram=$8.0 \cdot 10^{-5}$ mol/g; Mn≈50000 g/mol PDMS(5): Gelest; compound of formula (III) Mn≈30000 g/mol; amount of N—H bonds per gram=$1.33 \cdot 10^{-4}$ mol/g PDMS(6): Gelest; compound of formula (IV) amount of N—H bond per gram=$1.71 \cdot 10^{-3}$ mol/g;

PDMS(7): Gelest; compound of formula (IV) amount of N—H bond per gram=$2.43 \cdot 10^{-3}$ mol/g;

PDMS(8): Gelest; compound of formula (IV); amount of N—H bond per gram=$5.14 \cdot 10^{-3}$ mol/g;

PDMS(9): Gelest; compound of formula (V); amount of N—H bond per gram=$6.54 \cdot 10^{-3}$ mol/g;

PDMS(10): Gelest; compound of formula (V); amount of N—H bond per gram=$8.57 \cdot 10^{-4}$ mol/g;

PDMS(11): Bluestar Silicones; compound of formula (V) amount of N—H bond per gram=$3.21 \cdot 10^{-4}$ mol/g;

PDMS(12): Bluestar Silicones; compound of formula (V) with terminal units of dimethylmethoxysilyl instead of trimethylsilyl, amount of N—H bond per gram=$1.61 \cdot 10^{-4}$ mol/g Dynamic Viscosity:

The dynamic viscosity of the products was measured by means of a rheometer with imposed stress (TA-DHRII). The measurements were conducted in a flow mode with a cone/plane geometry with a diameter of 40 mm and having a truncation of 52 μm. The viscosity was recorded according to the shearing rate (0.01-100 s$^{-1}$) at 25° C.

NMR:

The nuclear magnetic resonance spectra $^1$H (NMR) were recorded on a spectrometer Bruker Avance III at 400 MHz. The samples were dissolved ether in deuterated chloroform, or in a CDCl$_3$/MeOD mixture (60/40 mol) and analyzed at 27° C.

Rheology:

Rheological analyses were conducted by means of a rheometer with imposed stress (TA-DHRII) at 25° C. by using a plane/plane geometry (diameter of 40 mm). The frequency sweeps were recorded in the linear viscoelastic domain of the products between 100 and 0.01 Hz.

Example 1: Preparation of the ORGANOSILOXANE (1)

THE ORGANOSILOXANE (1) was prepared according to the following procedure: N-(2-aminoethyl)-3-aminopropylmethyldimethoxysilane (5.0 g) and hexamethyldisiloxane (20.1 g) were mixed in a two-necked flask surmounted with a condenser in the presence of tetramethylammonium hydroxide dissolved in methanol (0.5 g). The reaction mixture was stirred with nitrogen sweeping at room temperature for 10 minutes and then was heated to 90° C. for 2 hours and then to 130° C. for 30 minutes. The reaction mixture was then cooled down to room temperature (20 to 25° C.) and the obtained product was purified by fractionated vacuum distillation. A fraction of 2.3 g corresponding to the ORGANOSILOXANE (1) is taken out at 106° C. at 0.41 mbars at the column head, the boiler being brought to 200° C. The yield of the reaction is 30%.

Example 2: Reaction of the ORGANOSILOXANE (1) with Acrylic Acid

In a two-necked flask, are mixed the ORGANOSILOXANE (1) and the acrylic acid. The ORGANOSILOXANE (1) and the acrylic acid are added in amounts such that r=0.33 and J=0.5. The mixture is put under magnetic stirring for 24 h at 50° C. at atmospheric pressure.

An $^1$H NMR analysis of the reaction medium sampled at 1, 4, 6, 8 and 24 h of reaction, gave the possibility of showing a disappearance of the acrylic functions over time. Without intending to be bound by any theory, this disappearance of the acrylic functions is due to the Aza-Michael reaction between the N—H bonds of the ORGANOSILOXANE (1) and the acrylic functions.

A test 3 was also carried out, identical with the test 2 (same proportion) but by replacing the ORGANOSILOXANE (1) by octamethyltrisiloxane. This test did not show the formation of a polymer of acrylic acid. This shows that the disappearance of the acrylic functions observed by NMR in test 2 is not due to a polymerization reaction of acrylic acid but actually to the Aza-Michael reaction between the N—H bonds borne by the ORGANOSILOXANE (1) and the double carbon-carbon bond of the acrylic acid.

Example 3: Influence of the Temperature on the Conversion of the Acrylic Acid

In three sealed pill boxes were mixed the ORGANOSILOXANE (2) and the acrylic acid (r=0.5, J=1). The reaction mixtures are maintained at a temperature of 25° C. (Test 5), 50° C. (Test 6) and 70° C. (Test 7). The conversion of the acrylic functions over time was followed with $^1$H NMR. The results are shown in the following table 1.

TABLE 1

| | TEST No. | | |
| --- | --- | --- | --- |
| | 5 | 6 | 7 |
| Time (h) | Conversion (%) | | |
| 0 | 0 | 0 | 0 |
| 1 | 16 | 39 | 84 |
| 2 | 18 | 54 | / |
| 4 | 23 | 71 | 98 |
| 6 | 27 | 81 | / |
| 7 | / | / | 100 |
| 8 | 32 | 86 | / |
| 24 | 55 | 98 | / |
| 48 | 73 | 100 | / |
| 49 | / | / | 100 |
| 168 | 94 | 100 | / |

These results show that by increasing the temperature it is possible to obtain a total conversion of the acrylic functions for 7 h at 70° C.

The obtained products were qualitatively analyzed in terms of viscosity, homogeneity, solubility, etc. The results show that the obtained products are homogeneous, soluble in chloroform, dispersible in water, more viscous than the initial ORGANOSILOXANE (2) and have a transparency equivalent to that of the initial ORGANOSILOXANE (2).

Example 4: Reaction of PDMS (3) with Bulk Acrylic Acid

In a one-neck flask of 15 mL, were mixed the PDMS (3) and the acrylic acid. The PDMS (3) and the acrylic acid are added in amounts such that r=0.5 and J=1. The reaction mixture was set with magnetic stirring for 72 h at a temperature of 50° C. No post-reaction treatment was applied. A $^1$H NMR analysis of the obtained product in CDCl$_3$ at 27° C. (128 scans) gave the possibility of showing a disappearance of the acrylic functions. The conversion was calculated, on the basis of $^1$H NMR, at 96%, at t=72 h.

The dynamic viscosities of PDMS (3), of the mixture PDMS (3) and the acrylic acid at t=0, and of the product obtained after 72 h of reaction were measured with different shear rates (0.1-100 s$^{-1}$) and are shown in the table 2 hereafter.

TABLE 2

| TEST No. | Products | Dynamic viscosity (mPa · s) |
| --- | --- | --- |
| 8 | PDMS (3) | 57.5 ± 6.5 |
| 9 | PDMS (3)/AA t = 0 | 1225 ± 50 |
| 9 | PDMS (3)/AA t = 72 h | $1.75 \cdot 10^5 \pm 5 \cdot 10^3$ |

These results show that the PDMS (3) initially has a low viscosity. The dynamic viscosity increases when the PDMS (3) is mixed with acrylic acid at t=0. Without intending to be bound by any theory, this increase in dynamic viscosity is due to the acid-base reaction between the amine functions of PDMS (3) and acrylic acid. The dynamic viscosity of the final product (product stemming from the Aza-Michael reaction between the PDMS (3) and acrylic acid after 72 h) is more than 100 times greater than that of the PDMS (3) and much greater than that of the mixture of PDMS (3) and acrylic acid at t=0. Without intending to be bound by any theory, and as shown by the results of Example 3, this increase in dynamic viscosity is due to the Aza-Michael reaction coupled with an acid-base reaction between the PDMS (3) and the acrylic acid.

Example 5: Variation in the Nature of the PDMS, of J and r

The PDMSes 4 to 11 and the acrylic acid were reacted in bulk, in the ratios described in the table 4 hereafter, in a suitable plastic container. The reaction mixture was homogenized by means of a planetary gear mixer at a high speed (2,750 revolutions per minute) for 2 minutes and 30 seconds. An exothermal reaction is visible during the homogeneization, this is why the products were cooled to −20° C. before being homogenized. Thus, the maximum temperature within the product does not exceed 25° C. After homogeneization, the products are left at room temperature for several days (>17 days). The reaction conditions for the different tests are gathered in the following table 3.

TABLE 3

| TEST No. | PDMS | r | J |
| --- | --- | --- | --- |
| 10 | PDMS (4) | 0.52 | 1 |
| 11 | PDMS (5) | 0.54 | 1 |
| 12 | PDMS (6) | 0.50 | 1 |
| 13 | PDMS (7) | 0.51 | 1 |
| 14 | PDMS (8) | 0.50 | 1 |
| 15 | PDMS (9) | 0.67 | 1 |
| 16 | PDMS (10) | 0.68 | 1 |
| 17 | PDMS (10) | 1.35 | 2 |
| 18 | PDMS (11) | 0.71 | 1 |

The obtained products were analyzed by $^1$H NMR after 17 days of reaction at room temperature (20-25° C.) which gave the possibility of calculating the conversion of the acrylic functions. The obtained products were also evaluated in terms of viscosity (visual observation) and of solubility in different solvents. The results of these analyses are grouped in the table 4 hereafter.

TABLE 4

| | | Solubility (10 g/L) | | | | |
| --- | --- | --- | --- | --- | --- | --- |
| TEST No. | Conversion (%) | CDCl$_3$ | H$_2$O | IPA | THF | MCH |
| 10 | 67 | S | — | — | — | — |
| 11 | 68 | S | — | — | — | — |

TABLE 4-continued

| TEST No. | Conversion (%) | Solubility (10 g/L) | | | | |
|---|---|---|---|---|---|---|
| | | CDCl$_3$ | H$_2$O | IPA | THF | MCH |
| 12 | 72 | S | — | — | — | — |
| 13 | 70 | S | — | — | — | — |
| 14 | — | I | D | D | — | — |
| 15 | — | I | I | I | I | I |
| 16 | 87 | S | I | — | S | S |
| 17 | 84 | S | I | — | S | S |
| 18 | 90 | S | I | — | S | S |

Captions:
S: soluble; I: insoluble; D: dispersible; —: non-tested
CDCl$_3$: deuterated chloroform; H$_2$O: water; IPA: Isopropanol; THF: Tetrahydrofurane, MCH: Methylcyclohexane.

The obtained products all have a viscosity at least 10 times greater than the respective initial PDMSes. A high conversion rate of the acrylic functions after 17 days was determined by $^1$H NMR for all the products which may be solubilized in deuterated chloroform. The variation in the nature of the PDMS and of the ratios r and J therefore give the possibility of adjusting the properties of the synthesized materials.

The viscoelastic properties of the products obtained for the tests 16, 17 and 18 were recorded by means of a rheometer with imposed stress. The initial viscoelastic properties of the PDMSes (10) and PDMS (11) were also measured. For this, the time-dependent change in the elastic (G') and viscous (G") moduli versus frequency was recorded in the following conditions:

Deformation (δ) of 0.1% applied for the test 16 and the PDMS (10), deformation (δ) of 0.03% applied for the test 17 and deformation (δ) of 0.2% applied for the test 18 and the PDMS (11).

The results obtained after 18 days of reaction are grouped in both following tables 5 and 6.

TABLE 5

| | TEST No. | | | | | |
|---|---|---|---|---|---|---|
| | PDMS (10) | | 16 | | 17 | |
| Frequency (Hz) | G' (Pa) | G" (Pa) | G' (Pa) | G" (Pa) | G' (Pa) | G" (Pa) |
| 100 | 3.6 · 10$^2$ | 1.7 · 10$^2$ | 2.2 · 10$^5$ | 3.9 · 10$^4$ | 2.6 · 10$^5$ | 4.9 · 10$^4$ |
| 10 | 7 | 45 | 1.7 · 10$^5$ | 4.8 · 10$^4$ | 1.9 · 10$^5$ | 4.2 · 10$^4$ |
| 1 | 1.3 | 5 | 8.3 · 10$^4$ | 5.3 · 10$^4$ | 1.2 · 10$^5$ | 5.3 · 10$^4$ |
| 0.1 | 1.1 | 0.5 | 1.9 · 10$^4$ | 2.6 · 10$^4$ | 3.9 · 10$^4$ | 4.2 · 10$^4$ |
| 0.01 | / | / | 1.3 · 10$^3$ | 5.7 · 10$^3$ | 4.8 · 10$^3$ | 1.1 · 10$^4$ |
| | Crossing G'/G" | | Crossing G'/G" | | Crossing G'/G" | |
| Frequency (Hz) | > 100 | | 0.2 | | 0.1 | |

TABLE 6

| | TEST No. | | | |
|---|---|---|---|---|
| | PDMS (11) | | 18 | |
| Frequency (Hz) | G' (Pa) | G" (Pa) | G' (Pa) | G" (Pa) |
| 100 | 2.1 · 10$^3$ | 4.2 · 10$^3$ | 1.2 · 10$^5$ | 1.8 · 10$^4$ |
| 10 | 1.4 · 10$^2$ | 6.5 · 10$^2$ | 9.6 · 10$^4$ | 2.6 · 10$^4$ |
| 1 | 4 | 76 | 4.9 · 10$^4$ | 2.8 · 10$^4$ |
| 0.1 | 0.2 | 8 | 1.7 · 10$^4$ | 1.5 · 10$^4$ |
| 0.01 | 0.2 | 0.9 | 3.4 · 10$^3$ | 5.3 · 10$^3$ |
| | Crossing G'/G" | | Crossing G'/G" | |
| Frequency (Hz) | >100 | | 0.6 | |

The results show that the crossing point G'/G" is at 0.2 Hz for test 16, at 0.1 Hz for test 17 and at 0.6 Hz for test 18. The three obtained products therefore behave as viscoelastic solids over a wide range of frequencies.

The results also show an increase in the viscosity of the products obtained in tests 16 and 17 relatively to PDMS (10) and in test 18 relatively to PDMS (11), this increase being due to the Aza-Michael reaction coupled with the acid-base reaction.

From these results it was able to be inferred, by calculation, the following complex viscosities shown in table 7 and 8.

TABLE 7

| | TEST No. | | |
|---|---|---|---|
| | PDMS (10) | 16 | 17 |
| Frequency (Hz) | η* (Pa · s) | | |
| 100 | 0.6 | 3.5 · 10$^2$ | 4.2 · 10$^2$ |
| 10 | 0.7 | 2.8 · 10$^3$ | 3.1 · 10$^3$ |
| 1 | 0.8 | 1.6 · 10$^4$ | 2.2 · 10$^4$ |
| 0.1 | 1.9 | 5.2 · 10$^4$ | 9.1 · 10$^4$ |
| 0.01 | / | 9.3 · 10$^4$ | 2.0 · 10$^5$ |

TABLE 8

| | TEST No. | |
|---|---|---|
| | PDMS (11) | 18 |
| Frequency (Hz) | η* (Pa · s) | |
| 100 | 7 | 2.0 · 10$^2$ |
| 10 | 11 | 1.6 · 10$^3$ |
| 1 | 12 | 9.0 · 10$^3$ |
| ..,1 | 13 | 3.6 · 10$^4$ |
| 0.01 | 15 | 1.0 · 10$^5$ |

The results show a decrease in the complex viscosity when the frequency increases.

Example 6: Reaction of the PDMS (3) with Acrylic Acid in the Presence of a Solvent (25° C.)

In an one-neck flask of 25 mL, are mixed the PDMS (3), the isopropanol (IPA, 33% by weight based on the total weight of PDMS (3) and of acrylic acid) and acrylic acid. The PDMS (3) and the acrylic acid are added in amounts such that r=0.5 and J=1. The reaction mixture is set under magnetic stirring at 25° C. for 7 days. A $^1$H NMR analysis of the obtained product in CDCl$_3$ at 27° C. (128 scans) gave the possibility of showing the disappearance of the acrylic functions. At t=42 h, the conversion was estimated on the basis of $^1$H NMR as 37%.

Example 7: Influence of the Solvent (50° C.)

The reaction set into play PDMS (3) and the acrylic acid used in Examples 5 and 7 in the same proportions (r=0.5, J=1). To the reaction medium, is either added or not a solvent (85 mol-%): tert-butanol, isopropanol/water solution (50/50 mol) or a saturated solution of ammonia/isopropanol and the mixture is set under magnetic stirring at 50° C. for 24 h. The conversion of the acrylic functions is followed by $^1$H NMR and the results are shown in table 9 below.

TABLE 9

| TEST No. | Reaction medium | Conversion (%) versus time (h) | | | | |
|---|---|---|---|---|---|---|
| | | 0 h | 1 h | 4 h | 8 h | 24 h |
| 9 | Bulk | 0 | 8 | 17 | 31 | 69 |
| 19 | Tert-Butanol | 0 | 5 | 12 | 25 | 64 |
| 20 | IPA/Water | 0 | 0 | 3 | 5 | 35 |
| 21 | Ammonia solution | 0 | 8 | 18 | / | 56 |

These data show, in combination with the results of Examples 2, 4 and 6, that the method of the invention may be applied in the presence of different solvents or in bulk.

Example 8: Reaction of the ORGANOSILOXANE (2) with 2-carboxyethylacrylate

In a sealed pill box, were mixed the ORGANOSILOXANE (2) and 2-carboxyethylacrylate in proportions such that r=0.5 and J=1. The mixture is put under magnetic stirring for 48 h at 50° C. at atmospheric pressure. A $^1$H NMR analysis of the reaction medium sampled at 1, 4, 7, 24 and 48 h of reaction, gave the possibility of showing a disappearance of the acrylic functions over time. Without intending to be bound by any theory, this disappearance of the acrylic functions is due to the Aza-Michael reaction between the NH bonds of the ORGANOSILOXANE (2) and the acrylate functions. At t=48 h, a conversion of the acrylate functions by a value of 96% is attained. The table 10 below groups the data in terms of conversion relatively to the reaction time.

TABLE 10

| Time (h) | Conversion (%) |
|---|---|
| 1 | 62 |
| 4 | 73 |
| 6.5 | 77 |

TABLE 10-continued

| Time (h) | Conversion (%) |
|---|---|
| 24 | 90 |
| 48 | 96 |

Example 9: Effect of the Temperature of the Method. Reaction Between an Organopolysiloxane (PDMS 12) and Itaconic Acid The PDMS (12) is an organopolysiloxane of the same overall formula as the compound (V) but with terminal units of dimethylmethoxysilyl instead of trimethylsilyl, and having an amount of N—H bonds per gram of $1.61 \cdot 10^{-4}$ mol/g.

Two reactions are applied, one at 50° C. according to the invention and one at 120° C. (comparative test). Itaconic acid is a solid which is not soluble in the PDMS (12) at room temperature (20-30° C.). It was solubilized beforehand in methanol.

Example 9-a 0.11 g of solubilized itaconic acid in 0.23 g of methanol, i.e. 0.008 moles of itaconic acid which corresponds to 0.0016 moles of acid function, were mixed with 15.00 g of PDMS (12) as described above, which corresponds to 0.0024 mol of N—H bonds and 0.0016 mol of amine functions. The PDMS (12) was cooled beforehand below 0° C. before adding the solubilized itaconic acid. The mixture was then homogenized by means of a planetary gear mixer for 5 minutes at 2,750 revolutions per minute, the maximum temperature within the mixture not exceeding 25° C. After homogeneization, the mixture was placed in the oven at a temperature of 50° C. for one week so that the Aza-Michael reaction takes place and that the methanol is gradually evaporated.

The obtained product is colorless, transparent, homogeneous and soluble in THF and in methylcyclohexane.

Example 9-b 0.11 g of solubilized itaconic acid in 0.23 g of methanol, i.e. 0.008 mol of itaconic acid which corresponds to 0.0016 moles of acid function, were mixed with 15.00 g of PDMS (12) as described above, which corresponds to 0.0024 mole of N—H bond and 0.0016 mole of amine functions. The reaction medium is placed for 4 h at 120° C. in a one-neck flask surmounted with a condenser.

The obtained product is slightly yellowish and is not soluble in THF, nor in methylcyclohexane.

Both obtained products did not have the same properties which shows that they are different.

Example 10: Synthesis of a Supramolecular Material 0.77 g of acrylic acid, i.e. 0.011 moles of acid function, were mixed with 100 g of PDMS (12) cooled beforehand to −20° C., with a structure as described in Example 10, which corresponds to 0.0161 mol of N—H bonds and 0.011 mol of amine functions (r=0.68 and J=1). The mixture was then homogenized by means of a planetary gear mixer for 5 minutes at 2,750 rpm, the maximum temperature within the mixture not exceeding 25° C. After homogeneization, the mixture was placed in the oven in a hermetic flask at a temperature of 50° C. for one week.

The obtained product is a transparent viscoelastic solid. This product swells in THF and methylcyclohexane. After adding a chaotrope agent (<1% by mass) which gives the possibility of breaking the ionic bonds within the material, the product is totally soluble thereby showing its supramolecular nature.

The obtained supramolecular product was also transformed as a film with a thickness of 1 mm under pressure for 48 h at 50° C. Specimens of the H3 type ($L_0$=17 mm, thickness of 1 mm, width=4 mm according to the ISO 37:2011 standard) are cut out by dye-stamping and are left for one day at 45%±5% of humidity and at 25° C.±1° C. Uniaxial tensile tests or cyclic tensile tests were carried out with a tensile machine MTS 2/m with a sensor of 10N and a drawing speed of 0.25 $s^{-1}$. The dependency of the mechanical properties with the drawing speed was achieved by varying the drawing speed from 0.08 s-1 to 0.42 s-1. The obtained tensile strength is around 0.2 MPa and the elongation at break is extremely high, of the order of 4,000%.

Example 11: Synthesis of a Charged Supramolecular Material

Example 10 was again conducted as described earlier. Directly after homogeneization of both compounds by means of a planetary mixer, 5% by weight of a hydrophobic pyrogenated silica (Aerosil® R104) was added and this mixture is again homogenized by means of the planetary gear mixer for 10 minutes at 2,750 rpm and then placed in the oven in a hermetic flacon at a temperature of 50° C. for one week.

As described earlier, specimens H3 were cut out from the obtained product, put in the form of a film beforehand. Tensile tests were carried out like in Example 11. The tensile strength is 0.5 MPa and the elongation at break is always very high, of the order of 2,000%.

The invention claimed is:

1. An organopolysiloxane (A), comprising a filler, which may be obtained by reaction, at a temperature comprised between 10 and 75° C., between:
    at least one compound (C) selected from the group consisting of the organic compounds comprising at least one alkene or alkyne function for which at least one of the substituents is an acid function and the organic compounds comprising at least one acid function and at least one alkene or alkyne function for which at least one of the substituents is an electroattractor group; and
    at least one organopolysiloxane (B) selected from the group consisting of the organopolysiloxanes comprising siloxyl units (I.1) and (I.2) of the following formulae:

$Y_a Z^1_b SiO_{\frac{4-(a+b)}{2}}$; and (I.1)

$Z^2_c SiO_{\frac{4-c}{2}}$ (I.2)

wherein:
    a=1 or 2, b=0, 1 or 2 and a+b=1, 2 or 3
    c=1, 2, 3 or 4
    the symbols Y, either identical or different, represent a functional group of formula (I.3):

-E-(NH-G)$_h$-(NH$_2$)$_i$ (I.3)

wherein:
    h=0 or 1;
    i=0 or 1;
    h+i=1 or 2;
    E represents an aliphatic, cycloaliphatic or aromatic divalent hydrocarbon comprising from 1 to 30 carbon atoms;
    when it is present, G represents an aliphatic hydrocarbon radical comprising from 1 to 10 carbon atoms, monovalent when i=0 or divalent when i=1;
    the symbols $Z^1$ and $Z^2$, either identical or different, represent a monovalent hydrocarbon radical having from 1 to 30 carbon atoms and optionally comprising one or several unsaturations and/or one or several fluorine atoms, a hydroxyl group, or a radical-$OR^1$ with $R_1$ which represents a linear, cyclic or branched $C_1$-$C_{10}$ hydrocarbon radical;
said polyorganosiloxane (B) comprising, per molecule, at least one siloxyl unit (I.1) bearing at least one functional group of formula (I.3),
    the reaction being made in the presence of a filler.

2. The organopolysiloxane (A) according to claim 1 wherein the temperature is comprised between 10 and 70° C.

3. The organopolysiloxane (A) according to claim 1, wherein the compound (C) is selected from among the organic compounds comprising at least a double carbon-carbon bond for which at least one of the substituents is a carboxylic acid function.

4. The organopolysiloxane (A) according to claim 1, wherein the compound (C) is selected from among the compounds of formula (II)

(II)

wherein:
    $R^2$, $R^3$ and $R^4$, either identical or different, represent a hydrogen atom, a COOH group or a $C_1$-$C_6$;
    $R^5$ represents a hydrogen atom, an alkyl group or an aryl group, wherein the alkyl and the aryl comprise at least one COOH group.

5. The organopolysiloxane (A) according to claim 1, wherein the compound (C) is selected from the group consisting of acrylic acid, methacrylic acid, itaconic acid, crotonic acid, 2-carboxyethylacrylate, 3-carboxypropylacrylate, maleic acid, fumaric acid, 2-(acryloyloxy)acetic acid, 2-(acryloyloxy)propanoic acid, 3-(acrylolyloxy)propanoic acid, 2-(acryloyloxy)-2-phenylacetic acid, 4-(acryloyloxy) butanoic acid, 2-(acryloyloxy)-2-methylpropanoic acid, 5-(acryloyloxy)pentanoic acid, (E)-but-2-enoic acid, (Z)-prop-1-ene-1,2,3-tricarboxylic acid, cinnamic acid, sorbic acid, 2-hexenoic acid, 2-pentenoic acid, 2,4-pentadienoic acid, ethenesulfonic acid, vinylphosphonic acid, (1-phenyl-vinyl)phosphonic acid, 3-(vinylsulfonyl)propanoic acid, 2-(vinylsulfonyl)acetic acid, 2-(vinylsulfonyl)succinic acid, acetylene dicarboxylic acid and propiolic acid.

6. The organopolysiloxane (A) according to claim 1, wherein the organopolysiloxane (B) is selected from the group consisting of the organopolysiloxanes comprising siloxyl units (I.1) and (I.2) of the following formulae:

$Y_a Z^1_b SiO_{\frac{4-(a+b)}{2}}$; and (I.1)

-continued

(I.2)

wherein:
Y and $Z^1$ and $Z^2$ are definitions given in claim 1;
a=1 or 2, b=0, 1 or 2 and a+b=2 or 3
c=1 or 2.

7. The organopolysiloxane (A) according to claim 1, characterized in that the organopolysiloxane (B) has a degree of polymerization comprised between 2 and 5,000.

8. The organopolysiloxane (A) according to claim 1, wherein the organopolysiloxane (B) has a dynamic viscosity measured at 25° C. with a rheometer with imposed stress comprised between 1 and 100,000 mPa·s.

9. The organopolysiloxane (A) according to claim 1, characterized in that its viscosity, measured at 25° C. with a rheometer with imposed stress, is at least 10 times greater than that of the organopolysiloxane (B).

10. A method for preparing an organopolysiloxane (A) comprising putting into contact at a temperature comprised between 10 and 75° C.:
at least one compound (C) selected from the group consisting of the organic compounds comprising at least one alkene or alkyne function for which at least one of the substituents is an acid function and the organic compounds comprising at least one acid function and at least one alkene or alkyne function for which at least one of the substituents is an electronattractor group; and at least an acid function, and
at least one organopolysiloxane (B) selected from the group consisting of the organopolysiloxanes comprising siloxyl units (I.1) and (I.2) of the following formulae:

$Y_aZ^1_bSiO_{\frac{4-(a+b)}{2}}$; and (I.1)

$Z^2_cSiO_{\frac{4-c}{2}}$ (I.2)

wherein:
a=1 or 2, b=0, 1 or 2 and a+b=1, 2 or 3
c=1, 2, 3 or 4
the symbols Y, either identical or different, represent a functional group of formula (I.3):

-E-(NH-G)$_h$-(NH$_2$)$_i$ (I.3)

wherein:
h=0 or 1;
i=0 or 1;
h+i=1 or 2;
E represents an aliphatic, cycloaliphatic or aromatic divalent hydrocarbon radical comprising from 1 to 30 carbon atoms;
when it is present, G represents an aliphatic hydrocarbon radical comprising from 1 to 10 carbon atoms, monovalent when i=0 or divalent when i=1;
the symbols $Z^1$ and $Z^2$, either identical or different, represent a monovalent hydrocarbon radical having from 1 to 30 carbon atoms and optionally comprising one or several unsaturations and/or one or several fluorine atoms, a hydroxyl group, or a radical-OR$^1$ with IV which represents a linear, cyclic or branched $C_1$-$C_{10}$ hydrocarbon radical;

said polyorganosiloxane (B) comprising, per molecule at least one siloxyl unit (I.1) bearing at least one functional group of formula (I.3),
the method being carried out in the presence of a filler.

11. The method according to claim 10, applied at a temperature comprised between 10 and 70° C.

12. The method according to claim 10, applied in bulk or in the presence of a solvent.

13. The method according to claim 10, wherein the obtained organopolysiloxane (A) has a dynamic viscosity, measured at 25° C. with a rheometer with imposed stress, at least 10 times greater than that of the organopolysiloxane (B).

14. The method according to claim 10, wherein the ratio r representing the ratio between the number of moles of alkene or alkyne function of the compound (C) for which at least one of the substituents is an electroattractor group or an acid function, and the number of moles of N—H bonds borne by the organopolysiloxane (B)

is comprised between 0.01 and 10.

15. The method according to claim 10, wherein the ratio J representing the ratio between the number of mole of acid functions of the compound (C) and the number of mole of the amine function of the organopolysiloxane (B)

is comprised between 0.01 and 20.

16. A composition K1 comprising at least one organopolysiloxane (A) according to claim 1, and at least one filler and optionally at least one other organopolysiloxane and/or one or several usual functional additives, and/or an organopolysiloxane comprising at least one carboxylic function and/or at least one organopolysiloxane (B) as defined in claim 1.

17. The use of A method of using at least one organopolysiloxane (A) according to claim 1, comprising using said at least one organopolysiloxane in wound care; for the encapsulation of electronic components; as coatings; as additives; for temporary printing, or for thin layer coating.

18. A method of using at least one organopolysiloxane (A) according to claim 1, comprising using said at least one organopolysiloxane in paints, coatings, adhesives, sealants, personal care, health care, textile treatment, electronics, automotive field, rubbers, or anti-foam compositions.

19. A composition X for the preparation of an organopolysiloxane (A) according to claim 1, comprising:
at least one compound (C) selected from the group consisting of the organic compounds comprising at least one alkene or alkyne function for which at least one of the substituents is an acid function and the organic compounds comprising at least one acid function and at least one alkene or alkyne function for which at least one of the substituents is an electroattractor group; and at least one organopolysiloxane (B) selected from the group consisting of the organopolysiloxanes comprising siloxyl units (I.1) and (I.2) of the following formulae:

$$Y_a Z^1_b SiO_{\frac{4-(a+b)}{2}}; \text{ and} \quad (I.1)$$

$$Z^2_c SiO_{\frac{4-c}{2}} \quad (I.2)$$

wherein:
- $a=1$ or $2$, $b=0$, $1$ or $2$ and $a+b=1$, $2$ or $3$
- $c=1, 2, 3$ or $4$
- the symbols Y, either identical or different, represent a functional group of formula (I.3):

$$-E-(NH-G)_h-(NH_2)_i \quad (I.3)$$

wherein:
- $h=0$ or $1$;
- $i=0$ or $1$;
- $h+i=1$ or $2$;
- E represents an aliphatic, cycloaliphatic or aromatic divalent hydrocarbon radical comprising from 1 to 30 carbon atoms;
- when it is present, G represents an aliphatic hydrocarbon radical comprising from 1 to 10 carbon atoms, monovalent when $i=0$ or divalent when $i=1$;
- the symbols $Z^1$ and $Z^2$, either identical or different, represent a monovalent hydrocarbon radical having from 1 to 30 carbon atoms and optionally comprising one or several unsaturations and/or one or several fluorine atoms, a hydroxyl group, or a radical-$OR^1$ with IV which represents a linear, cyclic or branched $C_1$-$C_{10}$ hydrocarbon radical;

said polyorganosiloxane (B) comprising, per molecule, at least one siloxyl unit (I.1) bearing at least one functional group of formula (I.3).

20. The organopolysiloxane (A) according to claim 1, wherein the filler is a mineral filler.

21. The organopolysiloxane (A) according to claim 10, wherein the filler is a mineral filler.

* * * * *